United States Patent [19]

Cohen et al.

[11] 3,980,722

[45]*Sept. 14, 1976

[54] PRODUCTION OF BROMOSTYRENE, DIBROMOSTYRENE AND ALKYL BROMIDES

[75] Inventors: Ella Cohen, Ramat Hasharon; Stephen Daren, Rehovot; Moshe Levy, Rehovot; David Vofsi, Rehovot, all of Israel

[73] Assignee: Yeda Research & Development Co. Ltd., Rehovot, Israel

[ * ] Notice: The portion of the term of this patent subsequent to Feb. 18, 1992, has been disclaimed.

[22] Filed: July 3, 1973

[21] Appl. No.: 376,171

[30] Foreign Application Priority Data
July 4, 1972 Israel...................................... 39817

[52] U.S. Cl............................. 260/650 R; 260/657
[51] Int. Cl.².......................................... C07C 25/28

[58] Field of Search........................ 260/650 R, 657

[56] References Cited
UNITED STATES PATENTS
3,867,468  2/1975  Vofsi et al...................... 260/650 R Primary Examiner—D. Horwitz
Attorney, Agent, or Firm—Hubbell, Cohen, Stiefel & Gross

[57] ABSTRACT

A process for the simultaneous production of bromostyrene or dibromostyrene and of an alkyl bromide, which comprises reacting bromoethyl bromobenzene or bromoethyl dibromobenzene with an alkanol at an elevated temperature. When only these reactants are reacted, the temperature is between 400°C and 550°C; when the reaction is effected in the presence of a source of free radicals, the temperature used can be lower, and temperatures of about 300°C are adequate.

6 Claims, No Drawings

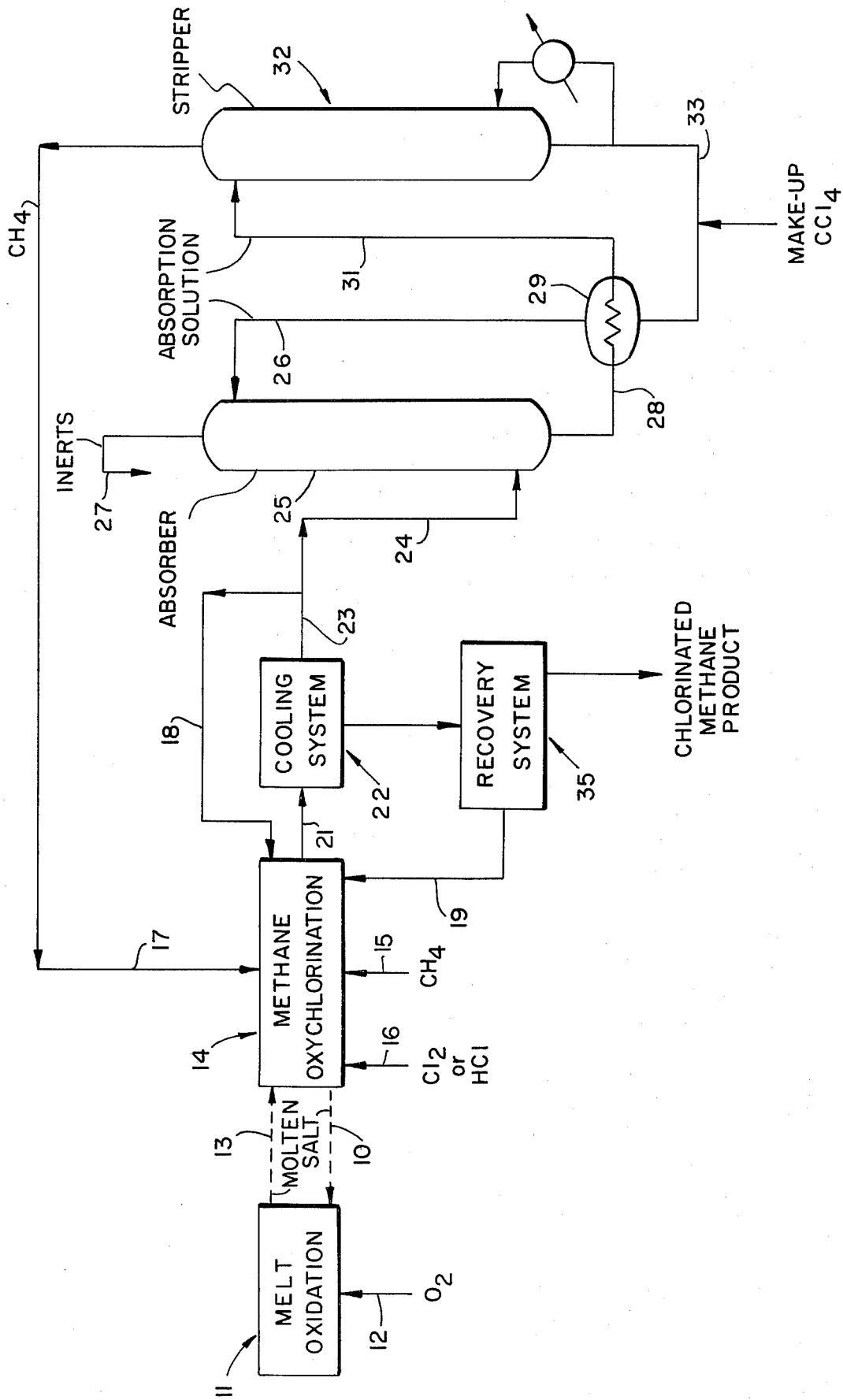

PURGING OF INERTS IN CHLORINATED HYDROCARBON PRODUCTION

The present invention relates to the production of chlorinated hydrocarbons, and more particularly, to a new and improved process for purging inerts from reaction systems employed for the production of chlorinated hydrocarbons.

In the production of chlorinated hydrocarbons, inerts such as nitrogen and/or carbon monoxide are generally present in the chlorinated hydrocarbon effluent. Accordingly, in order to prevent a build-up of such inerts in the system, there is a necessity to purge such inerts from the system.

The principle object of the present invention is to provide for purging of inerts from a system for producing chlorinated hydrocarbons.

In accordance with the present invention, there is provided a process for producing chlorinated hydrocarbons wherein a gaseous stream, containing unreacted hydrocarbon, and as inerts, carbon monoxide, nitrogen or mixtures thereof, is separated from a chlorinated hydrocarbon effluent, containing chlorinated hydrocarbons, unreacted hydrocarbon and the inerts. The gaseous stream is contacted with a liquid absorbent comprised of a chlorinated hydrocarbon having a number of carbon atoms equal to the hydrocarbon feed, to absorb unreacted hydrocarbon from the gaseous stream. The liquid absorbent, containing absorbed hydrocarbon, is separated from the gaseous stream and hydrocarbon stripped therefrom for ultimate recycle to the chlorinated hydrocarbon production zone. The gaseous stream of inerts may then be ultimately purged from the system.

The gaseous stream, containing unreacted hydrocarbon and inerts, may also include carbon dioxide and one or more chlorinated hydrocarbons, and in such a case, the chlorinated hydrocarbon(s) and carbon dioxide are also absorbed by the liquid absorbent. The chlorinated hydrocarbon(s) and carbon dioxide are also stripped from the liquid absorbent and may be recycled to the chlorinated hydrocarbon production zone along with the unreacted hydrocarbon or separately recovered whereby essentially only unreacted hydrocarbon is recycled to the chlorinated hydrocarbon production zone.

In general, only a minor portion of the gaseous stream containing hydrocarbon and inerts is subjected to the absorption operation in that treatment of a minor portion is generally sufficient to prevent a build-up of inerts in the system.

The absorption of the unreacted hydrocarbon and if present, carbon dioxide and chlorinated hydrocarbon(s), is generally effected at a temperature from about 80°F to about 200°F, preferably a temperature from about 100°F to about 130°F, and a pressure from about 50 psig to about 400 psig, preferably from about 150 psig to about 250 psig. The stripping of hydrocarbon, and if present, carbon dioxide and chlorinated hydrocarbon(s), from the absorption solution is generally effected at temperatures from about 180°F to about 200°F, preferably a temperature from about 185°F to about 225°F, and a pressure from about 1 psig to about 50 psig, preferably from about 5 psig to about 20 psig. It is to be understood that in the case where the absorption and stripping are effected in a column, as preferred, the reported temperatures are average temperatures for the column. It is also to be understood that the hereinabove described conditions are only illustrative of conditions generally employed and the selection of particular conditions for effecting the absorption and stripping are deemed to be within the scope of those skilled in the art from the teachings herein.

The gaseous stream, containing hydrocarbon and as inerts to be purged from the system, carbon monoxide and/or nitrogen, and which may further include carbon dioxide and one or more chlorinated hydrocarbons, to be employed as feed to the inert purging system may be separated from the chlorinated hydrocarbon effluent by any one of a wide variety of procedures. In general, the chlorinated hydrocarbon effluent also includes water vapor and a convenient method of separating the water vapor from the effluent gas is by cooling to condense water vapor therefrom, with such cooling also generally resulting in the condensation of heavier chlorinated hydrocarbon components from the gaseous effluent, whereby a gaseous stream containing unreacted hydrocarbon, inerts, carbon dioxide and generally also lighter chlorinated hydrocarbon(s), is recovered from the cooling operation. A portion of this gaseous stream may be employed as feed to the inert purging system. In general, such a gaseous stream can be recovered by cooling the chlorinated hydrocarbon effluent in one or more cooling stages (which can be indirect cooling stages or direct quench cooling) to a temperature from about 40°F to about 100°F, at pressures from about 190 psig to about 400 psig.

Although the above operation is preferred, it is to be understood that the gaseous stream containing unreacted hydrocarbon and inerts can be recovered by other means; e.g., fractionation. It is also to be understood that in such recovery operations, the gaseous feed to the inert purging system can be free of chlorinated hydrocarbon(s) and/or carbon dioxide; e.g., carbon dioxide can be recovered in a suitable carbon dioxide removal system such as an absorption system, prior to introduction of the gas containing unreacted hydrocarbon and inerts into the purging system.

The chlorinated hydrocarbon effluent may be produced by any one of a wide variety of processes known in the art, including both direct chlorination and oxidative or oxychlorination processes. In general, the direct chlorination processes can be effected in the presence or absence of a catalyst, whereas the so-called oxidative or oxychlorination processes are effected in the presence of a Deacon or oxychlorination type of catalyst. The general processes for producing chlorinated hydrocarbon by both chlorination and oxychlorination are well known in the art and no detailed description thereof is deemed necessary for a complete understanding of the present invention.

Although the process of the present invention is generally applicable to the chlorination and/or oxychlorination of hydrocarbons, the process is particularly suitable for the oxychlorination of $C_1$-$C_4$ aliphatic hydrocarbons (both saturated and olefinically unsaturated), and in particular, to the oxychlorination of methane to produce chlorinated methane(s); and ethane and/or ethylene to produce chlorinated $C_2$ hydrocarbons. In accordance with such a process, a molten mixture, containing cuprous chloride, cupric chloride and a suitable melting point depressant; in particular, potassium chloride, is contacted with molecular oxygen, in a first reaction (oxidation) zone, to produce copper oxychloride. A molten mixture, containing cuprous chloride, cupric chloride and copper oxychloride, withdrawn from the first reaction zone is contacted in a second reaction (oxychlorination and chlorination) zone with hydrocarbon and hydrogen chloride and/or chlorine to produce chlorinated hydrocarbon. The feed to the second reaction zone, as required, generally also includes chlorinated hydrocarbon as recycle. Molten salt from the second reaction zone is then recycled to the first reaction zone.

In general, the second reaction zone is operated at a temperature from 700°F to 1200°F, preferably 700°F to 950°F, with higher selectivity being obtained at temperatures from 700°F to 860°F, preferably 800°F to 850°F. The operating pressures are generally in the order of 1 to 10 atm.

The first reaction (oxidation) zone is generally operated at temperatures from 700°F to 950°F, and preferably from 800°F to 900°F, with the operating pressure generally being in the order of 1 to 10 atm.

The chlorinated hydrocarbons which are recycled to the oxychlorination reaction zone are determined by the desired reaction product. As should be apparent, if all chlorinated hydrocarbons are desired as product in the proportions produced there need be no recycle of chlorinated hydrocarbon. In the production, for example, of vinyl chloride by the use of ethane and/or ethylene, 1,2-dichloroethane produced in the oxychlorination is recovered and dehydrochlorinated in a separate reaction zone.

Particular processes for producing chlorinated methanes by the use of molten salts are described in U.S. Application Ser. No. 299,848, filed on Oct. 24, 1972, and U.S. Application Ser. No. 299,114, filed on Oct. 19, 1972, both of which are hereby incorporated by reference.

Particular processes for chlorination (oxychlorination) of ethane and/or ethylene by the use of molten salts are described in U.S. Application Ser. No. 153,374, filed on June 15, 1971 now Pat. No. 3,937,744 and U.S. Application Ser. No. 157,496, filed on June 28, 1971 now Pat. No 3,879,482 all incorporated by reference.

The invention will be further described with respect to an embodiment thereof illustrated in the accompanying drawing wherein:

The drawing is a simplified schematic flow diagram of an embodiment of the present invention.

Although the embodiment is particularly described with reference to the production of chlorinated methanes, the embodiment is equally applicable to the production of other chlorinated hydrocarbons.

Referring now to the drawing, a molten salt mixture including cuprous chloride, cupric chloride and a melting point depressant, in particular potassium chloride, in line 10, is introduced into an oxidation reaction zone 11 wherein the molten salt is contacted with molecular oxygen, introduced through line 12, to produce copper oxychloride.

A molten salt mixture, containing cuprous chloride, cupric chloride and copper oxychloride, withdrawn from oxidation zone 11, through line 13 is introduced into a methane oxychlorination reaction zone 14 wherein the molten salt is contacted with fresh feed methane, introduced through line 15, hydrogen chloride, chlorine or mixtures thereof, introduced through line 16, recycle methane streams, introduced through lines 17 and 18, obtained as hereinafter described, and a recycled chlorinated methane stream, introduced through line 19. As hereinafter described, as a result of such contact, methane is oxychlorinated to chlorinated methanes.

Molten salt recovered from the reaction zone 14 is recycled to oxidation reaction zone 11 through line 10.

A chlorinated methane effluent, containing chlorinated methanes, unreacted methane, water vapor, carbon dioxide, oxygen, and as inerts, nitrogen and carbon monoxide, is withdrawn from reactor zone 14 through line 21 and introduced into a cooling system, schematically indicated as 22. In the cooling system 22, the effluent is cooled in one or more stages to condense water vapor therefrom. In effecting such water condensation, heavier chlorinated methanes are condensed from the effluent and there is recovered a gaseous stream comprised of methane and lighter components (carbon monoxide, oxygen, carbon dioxide and nitrogen), which generally also includes some lighter chlorinated methane(s), generally methyl chloride, and some minor quantities of methylene chloride and chloroform (some small amounts of carbon tetrachloride could also be present) which is withdrawn from zone 22 through line 23.

The remainder of the chlorinated hydrocarbon effluent is withdrawn from zone 22 through line 24 and introduced into a recovery system to recover desired chlorinated methane product, and chlorinated methanes for recycle to the methane oxychlorination reaction zone through line 19.

A major portion of the gaseous stream in line 23 is recycled through line 18 to reaction zone 14. Alternatively, a portion of the gaseous stream in line 18 may be introduced into a carbon dioxide separation zone (not shown), prior to recycle to reaction zone 14, in order to prevent a build-up of carbon dioxide. As a further alternative, if there is to be no recycle of chlorinated methanes, the gaseous stream in line 18 may be introduced into the recovery system 35 wherein the chlorinated methanes are recovered, as product, and the unreacted methane is recovered for recycle. The recovery system 35 may also include carbon dioxide recovery to prevent a build-up thereof in the system.

A minor portion of the gaseous stream, containing methane, carbon dioxide, oxygen, inerts and some chlorinated methane(s), in line 24 is introduced into an absorption column 25 of the inert purging system wherein the gaseous stream is countercurrently contacted with an absorption liquid, which can be one or more of methylene chloride, chloroform or carbon tetrachloride, and particularly carbon tetrachloride, introduced through line 26. As a result of the countercurrent contact, methane, carbon dioxide and chlorinated methane(s) are absorbed from the gaseous stream.

A gaseous stream, comprised of the inerts, is withdrawn from column 25 through line 27 for purging from the system. The gas in line 27 may contain some minor quantities of methane and the heating value of such methane may be recovered, prior to purging the gas from the system.

The rich absorption solution, containing largely absorbed methane, carbon dioxide and chlorinated methane(s), with some nitrogen, oxygen and carbon monoxide, is withdrawn from column 25 through line 28, passed through heat exchanger 29 wherein the rich absorption solution is heated by indirect heat transfer with lean absorption solution, and introduced through line 31 into a stripping column 32, designed and operated to strip absorbed components from the absorption solution.

A lean absorption solution is withdrawn from stripper 32 through line 33, passed through heat exchanger 29 and introduced into absorption column 25 through line 26.

Components stripped from the absorption solution; in particular, methane, carbon dioxide and chlorinated methane(s), with some nitrogen, carbon monoxide and oxygen, are withdrawn from column 32 and recycled to reaction zone 14 through line 17. Alternatively, the stripped components can be introduced into the recovery system in order to separately recover methane for recycle to the reaction zone 14. Similarly, the stripped components can be introduced into a carbon dioxide removal zone prior to methane recycle. It should be apparent that several alternative procedures are possible with the methane stripped from the absorption solution ultimately being recycled alone or in combination with other components to reaction zone 14.

It is to be understood that the invention is not limited to the embodiment particularly described with reference to the drawing although such an embodiment is preferred. Thus, for example, the chlorinated methanes can be produced by a process other than molten salt oxychlorination as particularly described.

Similarly, a gaseous stream comprised of methane and inerts can be recovered other than by quenching and cooling as described; e.g., by fractionation.

Similarly, the gaseous stream introduced into the absorption system for purging inerts can be free of carbon dioxide and/or chlorinated methane(s); e.g., carbon dioxide can be removed from the stream prior to introduction into the absorption system and/or chlorinated methanes can be completely separated from the gaseous stream.

Although the process has been particularly described with respect to a process for producing chlorinated methanes, the process is also applicable to the production of other chlorinated hydrocarbons. Thus, for example, the process could be employed for the oxychlorination of ethane and/or ethylene; in which case, a $C_2$ chlorinated hydrocarbon would be employed as an absorption oil; e.g., one or more of dichloroethane, trichloroethylene, tetrachloroethylene or heavier chlorinated $C_2$ hydrocarbons. Accordingly, the chlorinated hydrocarbon absorption oil has a number of carbon atoms corresponding to the carbon atoms of the hydrocarbon which is oxychlorinated.

These and other modifications should be apparent to those skilled in the art from the teachings herein.

The invention will be further described with respect to the following example, however, the scope of the invention is not to be limited thereby.

EXAMPLE

| Conditions | Absorber (25) | Stripper (32)* |
|---|---|---|
| Temp. Top °F | 114 | 182 |
| bottom °F | 120 | 205 |
| Press. Top, PSIG | 175 | 7 |
| Bottom PSIG | 180 | 10 |
| Trays | 50 | 25 |
| Solvent | $CCl_4$ 900 GPM | $CCl_4$ |

| | ABSORBER FEED | | ABSORBER OVHD ("INERTS") | | STRIPPER OVHD COOLED* | | $CCl_4$ MAKE UP | |
|---|---|---|---|---|---|---|---|---|
| Component | LBMOL/HR | LB/HR | LBMOL/HR | LB/HR | LBMOL/HR | LB/HR | LBMOL/HR | LB/HR |
| $CH_4$ | 108.8 | 1741 | 7.6 | 122 | 101.2 | 1619 | | |
| $C_2H_4+C_2H_6$ | 0.2 | 6 | — | — | 0.2 | 6 | | |
| — | — | — | — | — | — | — | | |
| $N_2$ | 13.6 | 380 | 6.8 | 190 | 6.8 | 190 | | |
| $O_2$ | 2.4 | 76 | 1.2 | 38 | 1.2 | 38 | | |
| CO | 1.81 | 51 | 0.8 | 22 | 1.0 | 29 | | |
| $CO_2$ | 20.3 | 894 | — | — | 20.3 | 894 | | |
| $CH_3Cl$ | 23.5 | 1187 | — | — | 23.5 | 1187 | | |
| $CH_2Cl_2$ | 1.7 | 142 | — | — | 1.7 | 142 | | |
| $CHCl_3$ | 0.2 | 23 | — | — | 0.2 | 23 | | |
| $CCl_4$ | Nil | 3 | 0.7 | 105 | 3.0 | 467 | 3.7 | 569 |
| TOTAL | 172.5 | 4503 | 17.1 | 477 | 159.1 | 4595 | 3.7 | 569 |

*Overhead cooled externally to 40°F to minimize loss of $CCl_4$ solvent from the inerts removal system.

The present invention is particularly advantageous in that inerts are effectively purged from a chlorinated methane production system. The present invention is an improvement over the conventional flashing system for removing inerts in that hydrocarbon loss is minimized. In addition, costs are reduced in that there is no necessity for low level refrigeration. Furthermore, there is no necessity to initially separate carbon dioxide and/or chlorinated hydrocarbons prior to purging.

Numerous modifications and variations of the present invention are possible in light of the above teachings and therefore, within the scope of the appended claims the invention may be practiced otherwise than as particularly described.

What is claimed is:

1. In a process for producing chlorinated hydrocarbons wherein an effluent containing chlorinated hydrocarbons, unreacted hydrocarbon and inert gas selected from the group consisting of carbon monoxide, nitrogen and mixtures thereof is withdrawn from a chlorinated hydrocarbon production reaction zone, the improvement comprising:

recovering from the effluent a gaseous stream comprising unreacted hydrocarbon and said inert gas; contacting said gaseous stream with a liquid absorbent comprising a chlorinated hydrocarbon having a number of carbon atoms equal to the number of carbon atoms of the unreacted hydrocarbon to absorb unreacted hydrocarbon from said gaseous stream, said contacting being effected at a temperature of from 80°F to 200°F and a pressure of from 50 to 400 psig; separating the liquid absorbent containing absorbed unreacted hydrocarbon from the gaseous stream; stripping unreacted hydrocarbon from the liquid absorbent; and recycling stripped unreacted hydrocarbon to the reaction zone.

2. The process of claim 1 wherein the gaseous stream further comprises carbon dioxide, said carbon dioxide being absorbed with the unreacted hydrocarbon by the liquid absorbent.

3. The process of claim 2 wherein the gaseous stream further comprises at least one chlorinated hydrocarbon, said at least one chlorinated hydrocarbon being absorbed by the liquid absorbent with the unreacted hydrocarbon.

4. The process of claim 1 wherein the unreacted hydrocarbon is methane and said liquid absorbent comprises at least one member selected from the group consisting of methylene chloride, chloroform and carbon tetrachloride.

5. The process of claim 4 wherein the gaseous stream further comprises carbon dioxide and chlorinated methanes, said carbon dioxide and chlorinated methanes being absorbed by the liquid absorbent.

6. The process of claim 5 wherein the stripping is effected at a temperature of from 180°F to 280°F and a pressure of from 1 to 50 psig.

7. The process of claim 5 wherein the liquid absorbent is carbon tetrachloride.

8. The process of claim 1 wherein the unreacted hydrocarbon is a member selected from the group consisting of ethane, ethylene and mixtures thereof.

* * * * *

UNITED STATES PATENT OFFICE
CERTIFICATE OF CORRECTION

Patent No. 3,980,723　　　　　　　　　　Dated September 14, 1976

Inventor(s) Herbert Riegel

It is certified that error appears in the above-identified patent and that said Letters Patent are hereby corrected as shown below:

Column 1, line 63, "200°F" should be -- 280°F --.

Signed and Sealed this

Eleventh Day of January 1977

[SEAL]

Attest:

RUTH C. MASON　　　　　　　　　　C. MARSHALL DANN
*Attesting Officer*　　　　　　　　　　*Commissioner of Patents and Trademarks*